United States Patent
Maurice et al.

(10) Patent No.: US 12,059,306 B2
(45) Date of Patent: Aug. 13, 2024

(54) OPERATIVELY ADAPTIVE ULTRASOUND IMAGING SYSTEM

(71) Applicant: SUPERSONIC IMAGINE, Aix-en-Provence (FR)

(72) Inventors: François Maurice, Draguignan (FR); Frédéric Giral, Pourcieux (FR)

(73) Assignee: SUPERSONIC IMAGINE, Aix-en-Provence (FR)

( * ) Notice: Subject to any disclaimer, the term of this patent is extended or adjusted under 35 U.S.C. 154(b) by 18 days.

(21) Appl. No.: 16/628,760

(22) PCT Filed: Jul. 10, 2017

(86) PCT No.: PCT/IB2017/001033
§ 371 (c)(1),
(2) Date: Jan. 6, 2020

(87) PCT Pub. No.: WO2019/012303
PCT Pub. Date: Jan. 17, 2019

(65) Prior Publication Data
US 2020/0138414 A1    May 7, 2020

(51) Int. Cl.
*A61B 8/00* (2006.01)
*A61B 8/08* (2006.01)
*A61B 8/14* (2006.01)

(52) U.S. Cl.
CPC ............... *A61B 8/54* (2013.01); *A61B 8/145* (2013.01); *A61B 8/5207* (2013.01)

(58) Field of Classification Search
CPC ......... A61B 8/54; A61B 8/145; A61B 8/5207; A61B 8/44
See application file for complete search history.

(56) References Cited

U.S. PATENT DOCUMENTS 6,325,759 B1 * 12/2001 Pelissier ............... A61B 8/06
600/443
6,540,682 B1    4/2003 Leavitt et al.
(Continued)

FOREIGN PATENT DOCUMENTS

EP        3 117 774 A1    1/2017
EP        3117774  A1 *   1/2017 ........... A61B 8/4483
WO   2006/113335 A1    10/2006

OTHER PUBLICATIONS

International Search Report and Written Opinion, dated Apr. 6, 2018, from corresponding/related International Application No. PCT/IB2017/001033.

*Primary Examiner* — Joel Lamprecht
(74) *Attorney, Agent, or Firm* — NIXON & VANDERHYE

(57) ABSTRACT

An ultrasound imaging system includes an ultrasound probe including transducers, a digital acquisition board including electronic circuits adapted to control the transducers to emit ultrasound waves and to convert signals sensed by transducers into digital data; a real-time sequencer adapted to control the electronic circuits to drive the emission and reception of ultrasound signals, based on working parameters and sequence parameters; and a computer connected to the digital acquisition board and including a computer's memory, the parameters being stored in the computer's memory. The digital acquisition board further includes a DMA controller adapted to access the computer's memory in reading and writing by implementation of DMA protocols, and the sequencer is adapted to send requests to the DMA controller to recover the parameters from the computer's memory in real time.

15 Claims, 3 Drawing Sheets

(56) References Cited

U.S. PATENT DOCUMENTS

| | | | |
|---|---|---|---|
| 7,678,048 B1* | 3/2010 | Urbano | G01S 7/52046 |
| | | | 600/443 |
| 10,172,527 B2* | 1/2019 | Pernot | A61B 5/02007 |
| 2002/0007119 A1* | 1/2002 | Pelissier | A61B 8/565 |
| | | | 600/443 |
| 2005/0228281 A1 | 10/2005 | Nefos | |
| 2006/0042390 A1* | 3/2006 | Halvorsrod | G01S 7/5208 |
| | | | 73/606 |
| 2014/0347954 A1* | 11/2014 | Maurice | G01S 7/52017 |
| | | | 367/7 |
| 2016/0143624 A1* | 5/2016 | Liberman | A61B 8/481 |
| | | | 600/431 |
| 2016/0270763 A1 | 9/2016 | Hayes et al. | |

* cited by examiner

OPERATIVELY ADAPTIVE ULTRASOUND IMAGING SYSTEM

CROSS-REFERENCE TO RELATED APPLICATIONS

This application is a U.S. National Stage of international application PCT/IB2017/001033 filed Jul. 10, 2017.

FIELD OF THE INVENTION

The present invention concerns an ultrasound imaging system, a digital acquisition board part of said ultrasound imaging system, and an ultrasound imaging process.

BACKGROUND OF THE INVENTION

With reference to FIG. 1, an ultrasound imaging system is known, comprising:

- An ultrasound probe 1 comprising a plurality of transducers for emitting and receiving an ultrasound wave inside a medium, a received ultrasound wave being sensed by said transducers,
- A digital acquisition board 2, comprising electronic circuitry adapted to pilot said transducers for emitting ultrasound waves and to convert said sensed received ultrasound wave into input data, and
- A computer 3 receiving said input data through a data channel and processing these input data to provide an image representing a region of said medium, said processing being called beamforming.

According to this known imaging system, the electronic circuitry of the digital acquisition board 2 comprises at least an analog transmitter/receiver multiplexer 20 connected to the transducers, an emission processing chain 21, and a reception processing chain 22 comprising typically a plurality of variable gain amplifiers adapted to amplify the transducers signals, analog/digital converters adapted to convert amplified transducers signals into digital data, and a plurality of filters of variable gains and coefficients.

This electronic circuitry is driven by a sequencer 23 comprising main Field Programmable Gate-Array, driving a plurality of Field-Programmable Gate Array 24 (FPGA) or ASIC circuits distributed within the emission processing chain 21 and the reception processing chain 22.

In particular, in order to perform ultrasound imaging, the sequencer drives the electronic circuitry to perform sequences of alternating emission and reception events at a high frequency. For instance, the frequency of the emission events can reach about 10 kHz, with a reception event occurring between each emission events.

Each emission or reception event is performed according to specific working parameters and sequence parameters.

For instance, the working parameters comprise emission parameters related to the control of transducers for the emission of ultrasonic waves and reception parameters related to the processing of the received ultrasound waves sensed by the transducers.

The emission parameters can comprise waveforms of the emitted waves, whereas the reception parameters can comprise settings of the electronic circuitry including filters gains, demodulation frequency, multiplexer settings, etc.

The sequence parameters include instructions sent by the sequencer to each component of the electronic circuitry and timings for emission and reception processes.

All these parameters can vary for every event composed of one ultrasound wave emission and one ultrasound wave reception.

For instance, Doppler ultrasonography requires the emission of interleaved ultrasound waves of different frequencies, which itself requires changing all the emission and reception parameters between successive emission and reception events.

Moreover, these parameters vary according to the imaging mode that is implemented by the imaging system. For instance, the parameters of the ultrasonic waves sent by the transducers and the processing of the signals sensed by the transducers vary whether the imaging mode is Doppler ultrasonography, B-mode imaging, Shear Wave Elastography imaging, etc.

The sequencer 23 requires accessing all the working parameters and sequence parameters in real time to be able to drive the transducers and electronic circuitry to perform these sequences.

As the amount of parameters can be very large (up to tens of MegaBytes), the Digital Acquisition Board comprises a number of dedicated memories 25 storing all the working parameters and sequence parameters that the sequencer needs to access. For instance, the working parameters and sequence parameters corresponding to all the various imaging modes (B-mode, shear wave elastography, Doppler ultrasonography etc.) can be stored in the computer and, before beginning imaging according to a specific imaging mode, all the parameters related to this imaging mode are transmitted by the computer to the memories 25 of the Digital Acquisition Board, so that once an imaging sequence has begun, the sequencer has access to the parameters it needs, and can access those parameters each time a new image is created (for example from 20 to 100 times per second).

Therefore the memories 25 have the capacity of storing all the parameters relating to an imaging mode.

These memories can also store the input data converted by the electronic circuitry, also known as RF data, and which can be later transmitted to the computer for performing beamforming.

The memories 25 are distributed within the sequencer 23, the emission processing chain 21 and the reception processing chain 22 and are operated by corresponding FPGAs 23 and 24.

Another implementation of a known system comprising those additional memories is disclosed for instance in document WO2006/113445; the additional memories are referred to as "expansion memory" or "dual-port memory blocks".

The management of dedicated memories increases the computational resources required by the sequencer and therefore the sequencer comprises at least one central FPGA or ASIC circuit 23 for controlling the timing of the emission and reception events, and a plurality of additional FPGA or ASIC circuits 24 for sending emission and reception parameters to a number of transducers and the corresponding components of the electronic circuitry. For instance, the sequencer can comprise up to 9 FPGAs.

The system's cost and complexity are thus quite important.

In addition, since the user can only access the computer 3 and not directly and transparently the Digital Acquisition Board 2, it is not easy to change the parameters during real-time operation, for instance to immediately switch from one imaging mode to another, or to seamlessly change transmit focusing laws during real time operation.

OBJECTS AND SUMMARY OF THE INVENTION

Given the above, one aim of the present invention is to provide an ultrasound imaging system that solves the above technical problems.

In particular, one aim of the present invention is to simplify the ultrasound imaging system and make it cheaper.

Another aim of the present invention is to allow the user to change in real time the parameters during system operation, in order to allow adaptive operation of the system.

To this end, an ultrasound imaging system is disclosed, comprising:
an ultrasound probe comprising a plurality of transducers for emitting and receiving an ultrasound wave inside a region of a body,
a digital acquisition board comprising:
electronic circuits adapted to control the transducers to emit ultrasound waves and to convert signals sensed by transducers into digital data, and
a real-time sequencer adapted to control the electronic circuits to drive the emission and reception of ultrasound signals, based on working parameters of the electronic circuits and sequence parameters, and
a computer connected to the digital acquisition board and adapted at least for visualizing an image representing a portion of said region, the computer comprising a computer's memory,
wherein at least part of the working parameters and sequence parameters are stored in the computer's memory, the digital acquisition board further comprises at least one Direct Memory Access controller adapted to access the computer's memory in reading and writing by implementation of Direct Memory Access protocols,
and the real-time sequencer is adapted to send requests to the Direct Memory Access controller to recover said working parameters and sequence parameters from the computer's memory in real time.

Preferably, the ultrasound imaging system further comprises a PCI express bus connecting the computer to the digital acquisition board.

In embodiments, the electronic circuits comprise an emission processing chain comprising a transmission beamformer adapted to generate digital signals, and a pulser adapted to convert each digital signal into an electrical excitation of a transducer.

In embodiments, the electronic circuits comprise a reception processing chain comprising an analog processing chain, and a digital processing chain comprising at least an analog to digital converter.

Preferably, the working parameters comprise signal reception parameters including filtering coefficients, gains, demodulation frequencies, and time gain compensation profiles, and signal emission parameters including delays, signal waveforms, and apodization parameters.

In a particular embodiment, the working parameters comprise at least one library of predefined settings, said library being stored in a memory of the data acquisition board, and the addresses of the settings stored in the library being stored in the computer's memory, wherein the real-time sequencer is adapted to send requests to the Direct Memory Access controller to recover said addresses from the computer in real time, and the real-time sequencer is adapted to recover settings from the memory of the data acquisition board by indirection based on said addresses.

In an embodiment, at least one library stored in the data acquisition board comprises at least one of a library of waveforms for ultrasound emission, and a library of filters coefficients for received signals filtering.

Advantageously, the real-time sequencer comprises a single ASIC or FPGA including a software programmable processor.

In an embodiment, the computer's memory further stores the digital data converted by the electronic circuits.

In an embodiment, the computer further comprises a processor, the computer's memory stores beamforming parameters, and the computer's processor is adapted to perform the beamforming of the digital data.

Preferably, the at least one Direct Access Memory controller comprises one data import engine adapted to import data from the computer's memory by implementation of Direct Access Memory protocols, and one data export engine adapted to write data in the computer's memory by implementation of Direct Access Memory protocols.

A digital acquisition board is also disclosed, for use in an ultrasound imaging system, said ultrasound imaging system comprising:
an ultrasound probe comprising a plurality of transducers for emitting and receiving an ultrasound wave inside a region of a body,
a computer adapted at least for visualizing an image representing a portion of said medium, the computer comprising a memory,
the data acquisition board being located between the ultrasound probe and the computer and comprising:
electronic circuits adapted to control the transducers to emit ultrasound waves and to convert signals sensed by transducers into digital data, and
a real-time sequencer adapted to control the electronic circuits to drive the emission and reception of ultrasound signals, based on working parameters of the electronic circuits and sequence parameters,
wherein the data acquisition board further comprises at least one Direct Memory Access controller adapted to access the computer's memory in reading and writing by implementation of Direct Memory Access protocols,
and wherein the sequencer is to send requests to the Direct Memory Access controller to recover said working parameters and sequence parameters from the computer's memory in real time.

An ultrasound imaging process implemented by an ultrasound imaging system according to the above description is also disclosed, the ultrasound imaging process comprising alternative emission and reception sequences, wherein prior to each emission sequence, the real-time sequencer sends a request to the Direct Memory Access Controller to recover the working parameters and sequence parameters corresponding to the next emission and reception sequences in real time from the computer's memory.

In embodiments, the ultrasound imaging process comprises a change in the settings of an imaging mode during operation of the ultrasound imaging system, and the real-time sequencer recovering corresponding parameters prior to the next emission sequence.

In embodiments, the computer further comprises a controller, and the process further comprises the controller performing beamforming of the data received and processed by the digital acquisition board.

The ultrasound imaging system according to the invention exhibits simplified operation since the sequencer of the digital acquisition board can access any parameter required for operation of the system in real time by Direct Memory Access to the computer's memory.

This in particular allows a user to switch between imaging modes during operation since the sequence can access the different parameters related to the different imaging modes in real times.

The ultrasound imaging system according to the invention also exhibits a simplified structure as compared to the prior art, since it reduces the need for dedicated memories in the digital acquisition board, as some parameters are stored in the computer's memory instead of being stored in said dedicated memories. The diminution of dedicated memories in turn reduces the number of I/O pins (up to 200 I/O pins by memory module in the prior art) and the computational needs of the sequencer. In some embodiments the sequencer can comprise a single FPGA devoid of any additional external memory hardware.

Another advantage of the invention is that since the parameters are resident in the computer's memory, they can be easily modified in real time by the computer during system operation, allowing for adaptive operation during live operation.

BRIEF DESCRIPTION OF THE DRAWINGS

Other features and advantages of the invention will be apparent from the following detailed description given by way of non-limiting example, with reference to the accompanying drawings, in which.

DETAILED DESCRIPTION OF AT LEAST ONE EMBODIMENT OF THE INVENTION

Ultrasound Imaging System

Figure 1:
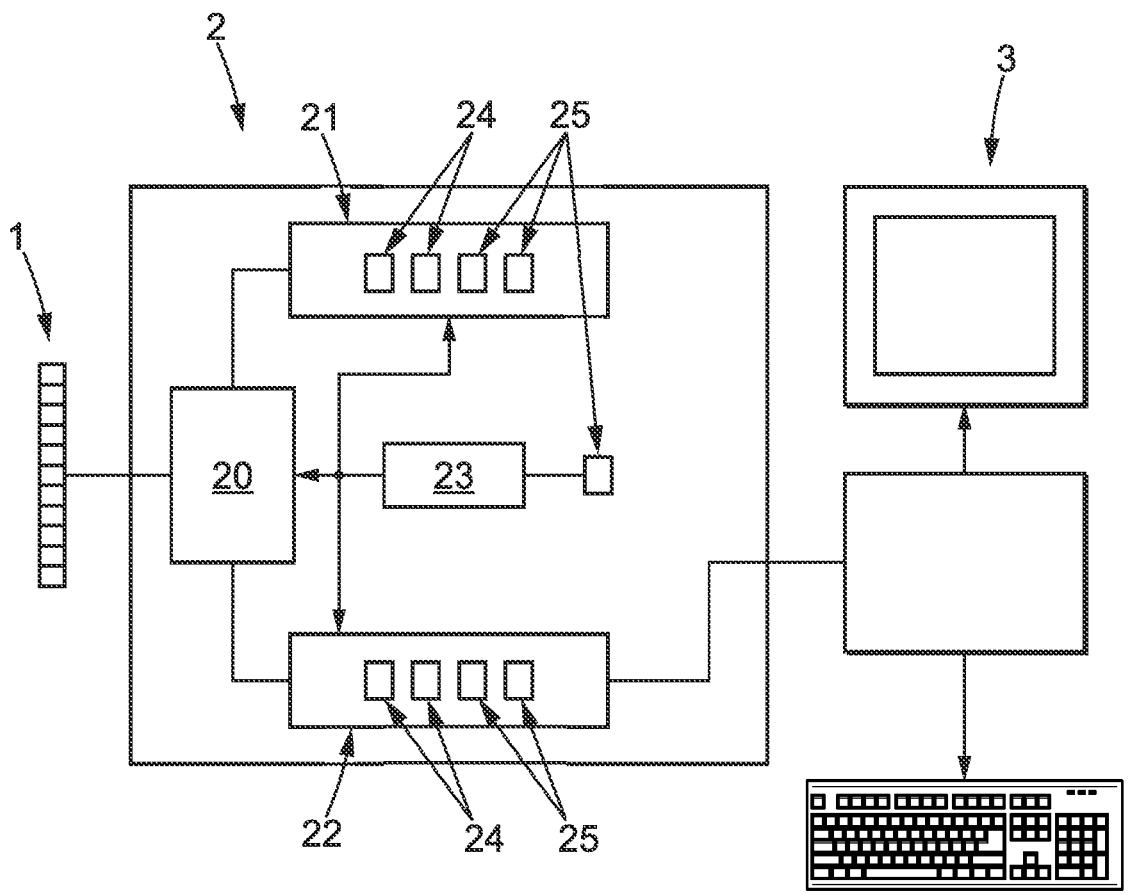
FIG. 1, already described, shows an exemplary ultrasound imaging system according to the prior art, FIG. 2 schematically discloses an exemplary structure of an ultrasound imaging system according to an embodiment of the invention.
Figure 2:
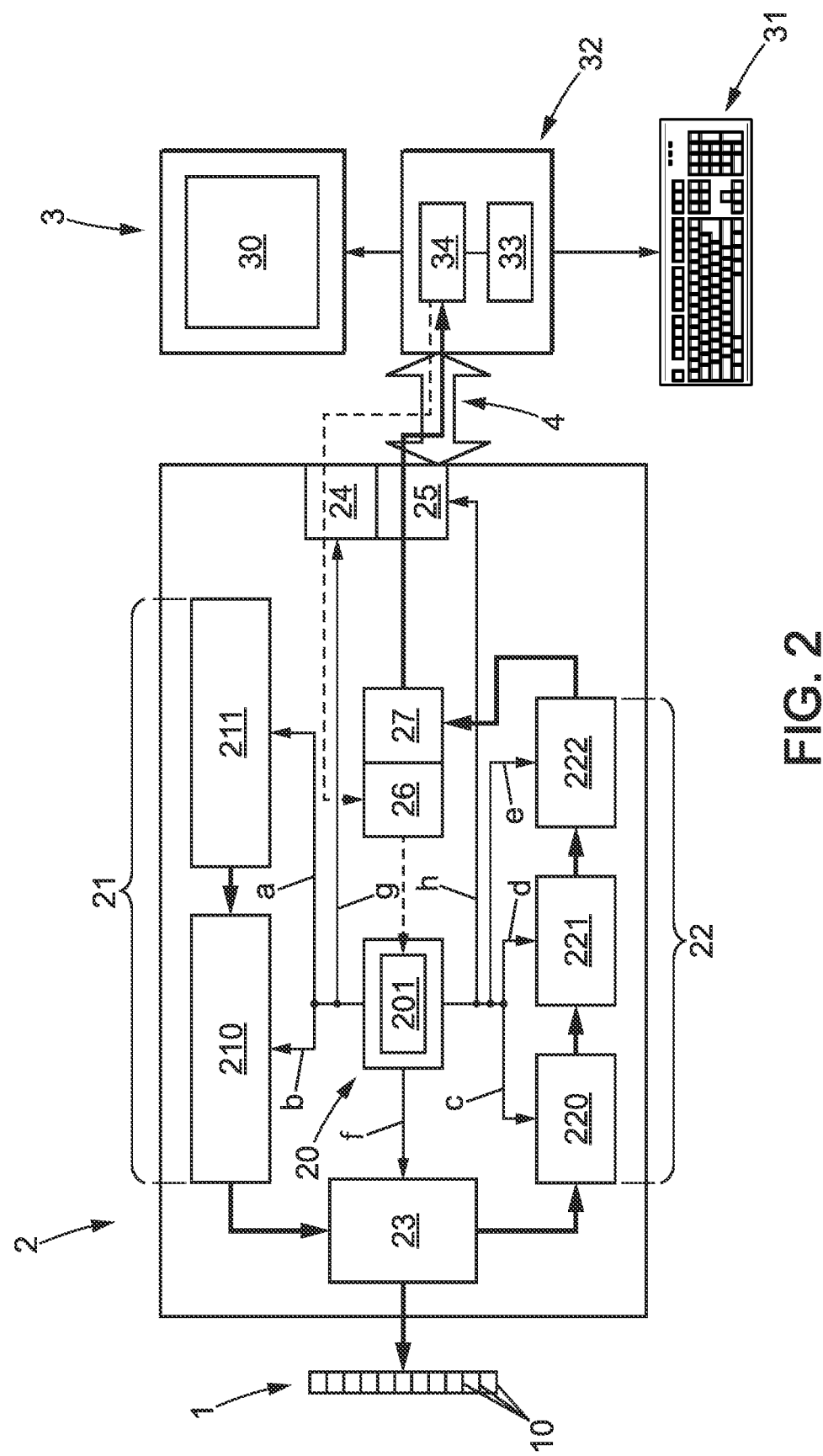

With reference to FIG. 2, an exemplary structure on an ultrasound imaging system is disclosed. This ultrasound imaging system is used for ultrasound imaging of a region, the region being typically living tissues of a body, preferably human tissues of a patient or tissues of an animal.

This system comprises an ultrasound probe 1, comprising a plurality of ultrasound transducers 10. The probe can be a linear array of transducers comprising typically tens of transducers, for instance between 100 and 300 transducers aligned along an axis. This probe can be used for bidimensional imaging. Alternatively, the probe can be a bidimensional array of transducers to perform a 3D imaging of the region.

The ultrasound imaging system 1 further comprises a digital acquisition board 2 described in more details thereafter, and connected to the ultrasound probe 1. The digital acquisition board pilots the transducers to emit ultrasound waves within the region according to specific parameters, and processes the ultrasound echoes sensed by the transducers into digital data that can then be beamformed and displayed as images. Said digital data are called RF data (before demodulation) or IQ data (after demodulation).

The ultrasound imaging system 1 also comprises a computer 3 for controlling the digital acquisition board 2 according to one or several imaging modes such as B-mode, Doppler ultrasonography, shear wave elastography, etc., and for viewing images obtained from the digital acquisition board 2. To this end, the computer 3 preferably comprises a screen 30, a Human-Machine Interface 31 allowing a user to enter instructions to the computer. The Human-Machine Interface can for example comprise a keyboard and/or a mouse or track ball. Alternatively the Human-Machine Interface can also comprise a tactile screen. In that case the screen 30 can be used both as a display and a Human-Machine Interface or the system may comprise a display screen 30 and an additional touch screen (not shown).

The computer 3 further comprises a central unit 32 comprising a controller 33 and a memory 34. The controller 33 may be for instance a processor or microprocessor.

The controller 33 is preferably configured to perform beamforming of the RF data obtained at the digital acquisition board.

Also, the memory 34 is preferably dimensioned to store both RF data transmitted by the Digital Acquisition Board 2, and images resulting from the beamforming.

The ultrasound imaging system preferably also comprises a PCI express bus or equivalent high speed bus (for example USB3) 4 connecting the Digital Acquisition Board 2 to the computer 3, in order to allow sufficient speed and bandwidth of the connection to ensure proper operation of the system.

Digital Acquisition Board

Still referring to FIG. 2, the Digital Acquisition Board 2 comprises electronic circuits adapted to control the transducers 10 to emit ultrasound waves, and to convert signals sensed by the transducers into digital data called RF data or IQ data. The Digital Acquisition Board 2 also comprises a real-time sequencer 20. The real-time sequencer 20 comprises at least one calculator 201, which is preferably a Field-Programmable Gate Array (FPGA) adapted to operate in real-time. In an embodiment, the real-time sequencer 20 comprises a single FPGA.

The real-time sequencer 20 controls the components of the electronic circuits, through control buses.

This control is performed by transmitting, to each component of the electronic circuits, sequence parameters regulating the timing of the ultrasound emission and reception events, and working parameters for tuning the components to emit ultrasounds and process ultrasound echoes according to a specific imaging mode.

On FIG. 2, thin lines represent the control buses through which the sequencer controls the electronic circuits. Dotted lines represent the path of data used by the sequencer, and thick solid lines represent the path of the ultrasound data which is described in more details hereinafter.

The electronic circuits of the digital acquisition board 2 comprise an emission processing chain 21 which is adapted to generate and transmit instructions to the transducers 10 for emitting ultrasounds of desired shapes and according to desired timings.

To this end, the emission processing chain comprises a high voltage pulser 210, which is a stage of power electronics generating, for each transducer 10, an electrical excitation which the transducer then converts into an ultrasound wave. This pulser 210 is controlled by a transmission beamformer 211 which generates electronic signals according to the waveforms and timing of the ultrasounds to be emitted, said waveforms and timing being transmitted by the sequencer 20 (arrow a).

Some parameters of the pulser 210 can also be tuned by the sequencer 20 (arrow b), such as for instance output impedance, instructions for activating or deactivating some channels of the pulser, etc.

The electronics circuits of the digital acquisition board 2 also comprise a reception processing chain 22 which is adapted to generate, from ultrasound echoes received by the transducers 10, RF data which can be then beamformed in order to generate images interpretable by an operator.

The reception processing chain 22 for example comprises an analog reception chain 220 which can comprise, for each reception channel (corresponding to a respective transducer 10 of the probe):
- A low noise amplifier (not shown)
- A variable gain amplifier (not shown)
- Fixed fain amplifiers (not shown)
- Analogical filters (not shown), with cut frequency that can be fixed or variable, and
- An anti-aliasing low-pass filter (not shown) at the output of the analog reception chain 220.

The components of this analog reception chain 220 operate based on working parameters such as gains, cut frequencies, etc. which are transmitted by the sequencer 20 (arrow c).

The reception processing chain 22 further comprises a digital reception chain 221, which can comprise at least one analog to digital converter, and optionally a digital demodulator and digital filtering circuits (not shown). The components of this digital reception chain 221 also operate based on working parameters such as gains and cut frequencies, demodulation frequency and filtering coefficients transmitted by the sequencer 20 (arrow d).

The analog and digital reception chains 220, 221 can optionally be implemented on one or several common chip(s), each chip being configured to process a number of channels, for instance 8, 16 or 32 channels simultaneously.

In some embodiments where the data beamforming is not performed at the computer but instead performed by the digital acquisition board, the reception processing chain 22 may comprise beamforming hardware 222 which is configured to perform beamforming on the RF data. In that case the beamforming parameters depending on the imaging mode may also be transmitted by the sequencer 20 (arrow e).

The Data Acquisition Board 2 also comprises a transmission and reception switch 23, which is connected to both the emission processing chain 21 and the reception processing chain 22, and is adapted to direct successively signals from the emission processing chain 21 towards the transducers, and ultrasound echoes received by the transducers towards the reception processing chain 22. The switch 23 is either passive, or active and controlled either by the pulser 220 or the sequencer 20 (arrow f).

Real-Time Operation of the Digital Acquisition Board

At least part of the working parameters tuning the components of the electronic circuits and transmitted by the sequencer, and of the sequence parameters defining the timings of the processing, also transmitted by the sequencer, are stored in the memory 34 of the computer 3, in order to lower the amount of data stored in the Digital Acquisition Board 2.

During operation of the ultrasound imaging system, the parameters stored in the computer's memory 34 are accessed in real time by the real-time sequencer 20, for each transmission and reception event, that is to say at a repetition frequency of around 10 kHz or lower.

To this end, the digital acquisition board 2 comprises at least one Digital Memory Access Controller which is adapted to access the memory of the computer in reading and writing in real time, through implementation of Direct Memory Access (DMA) Protocols. Implementation of DMA protocols allow accessing directly the memory 34 of the computer 3 in order to recover data stored therein, without involving the computer processor which generally does not operate in real time, because the most widespread operating systems of computers are not real time operating systems.

The Digital Acquisition Board preferably comprises one DMA controller 24 being a data import engine, adapted to access the memory 34 in reading, said controller 24 being adapted to recover the working parameters and sequence parameters stored in the memory 34 for each emission and reception event.

Preferably, the digital acquisition board also comprises at least one DMA controller 25, being a data export engine, adapted to access the memory 34 in writing in order to store the RF data processed after each reception event in the memory 34 of the computer. Therefore the RF data needs not be stored in the Digital Acquisition Board 2 prior to being transferred to the computer for beamforming, and the memory needs of the Digital Acquisition Board 2 can be reduced.

In the case where the Digital Acquisition Board 2 comprises beamforming hardware 222 performing beamforming on RF data, then the DMA controller uses DMA protocols to store the beamformed data in the computer's memory.

The real-time sequencer sends requests to each of the DMA controllers 24, 25 (respectively lines g and h on FIG. 2) for reading or writing data in the memory 34. Said requests in particular comprise the addresses that have to be accessed in the computer's memory 34, so-called "scatter gather list".

Last, the Digital Acquisition Board 2 also comprises a sequencer buffer memory 26 which is sized to store the working parameters and sequence parameters of a single or of few successive emission or reception events. The memory capacity of this buffer 26 is at least 10 times, and up to thousands times below the memory capacity of the dedicated memories used in the prior art for storing all parameters related to an imaging mode.

Thus, parameters obtained by the DMA controller 24 from the computer's memory are temporarily stored in the buffer memory 26, and once these parameters have been transmitted by the real-time sequencer to the components of the electronic circuits, they are erased from the buffer memory 26 by new parameters called from computer memory 34 for the next event(s).

The Digital Acquisition Board 2 also comprises a data buffer memory 27 which is sized to temporarily store RF data before sending them to the computer's memory by the DMA controller 25, in case of discrepancies between the data rates of the reception events and the transfer to the computer's memory.

Given the limited memory needs of the Digital Acquisition Board that are obtained thanks to the invention, the buffer memories 26 and 27 are preferably implemented within the internal memory of the FPGA of the real-time sequencer 20, therefore no additional memory chip than the internal memory already provided by the real-time sequencer 20 is needed in the Digital Acquisition Board 2.

The real-time sequencer 20 is also adapted to handle the priorities in accessing the buffer memories from either the sequencer 20, the DMA controllers 24, 25 and the reception processing chain 22.

For instance, the real-time sequencer 20 may preferably detect overflow of the buffer memories 26, 27 and consequently generate message or instructions to overcome this overflow (for instance skip an image, etc.)

Contrary to the prior art, once the parameters are recovered by the real-time sequencer, they are not stored in a dedicated memory of the digital acquisition board for a full period of operation according to a specific imaging mode. By contrast, the parameters are accessed in the memory of the computer for each transmission and each reception event, then transmitted once by the real-time sequencer 20 to the corresponding components of the electronics circuits, then erased from the buffer memory 26.

Therefore no memory other than the buffer memories 26, 27 is needed to store the data needed for operating the imaging device. In addition, the reduction in the number of memories in the Digital Acquisition Board reduces the need for FPGA I/O pins to connect memory modules as well as computational resources of the real-time sequencer. Hence the number of FPGAs comprised in the sequencer can be reduced, down to a single FPGA.

Another interesting result of the above-described imaging system is that the operator of the computer can also order, through the computer, a change in the parameters of the imaging mode, during real-time sequencer execution, in order to improve the image quality and perform adaptive operation of the imaging device. In that case, adjusting the parameters of the imaging mode only requires changing the parameters that are accessed in the computer's memory 34 by the sequencer (namely changing the address in the memory accessed by the sequencer).

Figure 3:
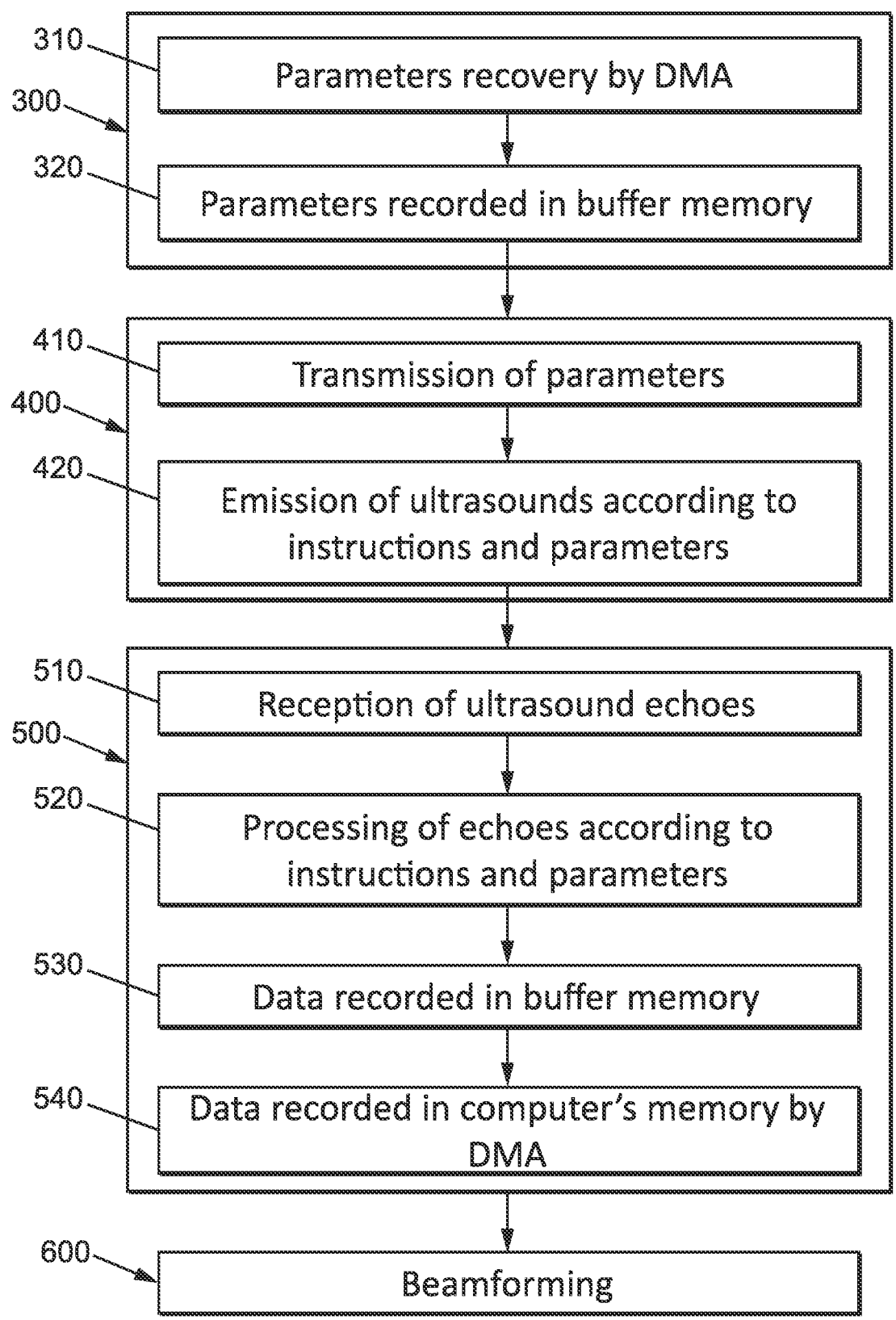
FIG. 3 represents the main steps of a process according to an embodiment of the invention.

This is shown in FIG. 3 which represents an exemplary embodiment of an imaging process performed by the imaging system described hereinabove.

The exemplary process shown in FIG. 3 comprises a firing sequence 400 followed by a reception sequence 500 of ultrasounds. The operation of the device comprises the succession of alternating firing and reception sequences.

Preliminarily to each firing and reception sequence, the process comprises a step 300 of loading the parameters necessary for performing the firing and reception sequences. Preferably, this step is performed in a time interval of 5 to 10 microseconds between a previous reception sequence 500 and a following firing sequence 400.

During a substep 310, the sequencer sends a request to the data import engine 24 to recover working parameters and sequence parameters corresponding to a selected imaging mode from the computer's memory, and the data import engine accesses said parameter by DMA in the memory 34. The recovered parameters relate both to the firing sequence and the reception sequence immediately following the firing sequence.

During a substep 320, the data import engine 24 records the parameters in the buffer memory 26.

The firing sequence 400 then comprises a substep 410, during which the real-time sequencer 20 transmits to each component of the emission processing chain 21 and, in an embodiment, to the transmission/reception switch 23, the instructions and parameters necessary to pilot the transducers to generate ultrasound echoes in the region. During this step, the real-time sequencer 20 also transmits the instructions and parameters to the reception processing chain 22 necessary to perform the processing of the ultrasound echoes.

Then emission processing chain 21 and the transducers operate according to the instructions and parameters to generate ultrasound echoes during a substep 420.

A reception sequence 500 comprises a step 510 of receiving, by the transducers, ultrasound echoes propagated within the region, and transmitting said echoes to the reception processing chain 22.

During a step 520, the components of the reception processing chain 22 perform a processing of the ultrasound echoes into RF data (or as the case may be, into beamformed data), according to the instructions sent by the real-time sequencer.

During a step 530, the RF data (or beamformed data) is recorded in the buffer memory 27, thereby erasing the data previously recorded in this memory 27.

During a step 540, the data export engine 25 records, in the computer's memory 34, the data stored in the buffer memory 27 by DMA as soon as this data is recorded in the buffer memory.

In an embodiment where beamforming of the RF data is performed by the computer, said beamforming is performed later in a step 600.

In case of a change in the settings of an imaging mode during operation of the system, for instance when an operator prompts instructions to obtain specific image settings, or in case of an auto-adaptive optimization process of the images, instructions are transferred by the computer's processor 33 to the real-time sequencer 20, which in the next recovery step 300 changes the parameters accessed in the computer's memory according to the new settings.

In some embodiments, all the working parameters and sequence parameters can be stored in the computer's memory.

In another embodiment, some parameters may remain stored in a memory of the Digital Acquisition Board. In particular, some working parameters can comprise libraries of predefined settings, which can for instance depend on the selected imaging mode, and remain constant during all the emission and reception events of a given imaging mode.

For example, there can exist a finite number of waveforms, corresponding to respective imaging modes, which are transmitted by the real-time sequencer and which define the electrical signals generating by the transmission beamformer 211. According to another example, a library comprising sets of filters numerical coefficients used in the various components of the reception processing chain 22 according to the various imaging modes can be established.

In that case, the library comprising the working parameters can be stored in the internal memory of a FPGA of the real-time sequencer, or of the transmission beamformer 211 or of one of the components 220, 221, 222 of the reception processing chain 22, as it only requires limited memory capacity (about tens of kilobits). The real-time sequencer 20 then accesses, in the computer's memory 34, the address of the specific parameter of the library that is needed for a given emission or reception event, and then accesses said parameter by indirection in the FPGA's memory.

The invention thus allows using the memory of a computer without involving the operation delays of a computer. This simplifies the cost and structure of a digital acquisition board, while allowing adaptive operation of the imaging system.

The invention claimed is:

1. An ultrasound imaging system, comprising:
    an ultrasound probe comprising a plurality of transducers configured to emit and receive an ultrasound wave inside a region of a body;
    a digital acquisition board comprising:
        electronic circuits configured to control the transducers to emit ultrasound waves and to convert signals sensed by transducers into digital data,
        a real-time sequencer configured to
            store a selected imaging mode of a plurality of imaging modes, and
            control the electronic circuits to drive the emission and reception of ultrasound signals, based on working parameters of the electronic circuits and sequence parameters regulating timing of the emission and reception of the ultrasound signals of the selected imaging mode, the working parameters comprising emission parameters related to the control of the transducers for the emission of the ultrasonic waves and reception parameters related to processing of received ultrasound waves sensed by the transducers for the selected imaging mode, at least one Direct Memory Access controller, and at least one buffer memory of the digital acquisition board; and a computer connected to and separate from the digital acquisition board and configured to visualize an image representing a portion of said region, the computer comprising a processor and a memory storing respective working parameters and sequence parameters of the plurality of respective imaging modes, wherein the at least one Direct Memory Access controller is configured to access the memory of the computer in reading and writing by implementation of Direct Memory Access protocols, and wherein the real-time sequencer is configured to send requests to the Direct Memory Access controller to cause the Direct Memory Access controller to recover a portion of the stored working parameters and the stored sequence parameters related to the selected imaging mode directly from the memory of the computer in real time without involving the processor of the computer, temporarily store the recovered portion of the working parameters and the sequence parameters of the selected imaging mode in the at least one buffer memory of the digital acquisition board, and transmit the temporarily stored working and sequence parameters of the selected imaging mode from the at least one buffer memory of the digital acquisition board to the electronic circuits, wherein the temporarily stored working and sequence parameters stored in the at least one buffer memory are overwritten by subsequent working and sequence parameters recovered from the memory of the computer by the DMA controller.

2. The ultrasound imaging system according to claim 1, further comprising a PCI express bus connecting the computer to the digital acquisition board.

3. The ultrasound imaging system according to claim 1, wherein the electronic circuits comprise an emission processing chain comprising a transmission beamformer configured to generate digital signals, and a pulser configured to convert each of the digital signals into an electrical excitation of a transducer of the plurality of transducers.

4. The ultrasound imaging system according to claim 1, wherein the electronic circuits comprise a reception processing chain comprising an analog processing chain, and a digital processing chain comprising at least an analog-to-digital converter.

5. The ultrasound imaging system according to claim 1, wherein the working parameters comprise signal reception parameters including filtering coefficients, gains, demodulation frequencies, and time gain compensation profiles, and signal emission parameters including delays, signal waveforms, and apodization parameters.

6. The ultrasound imaging system according to claim 1, wherein the working parameters comprise at least one library of predefined settings, said library being stored in a memory of the digital acquisition board, and the addresses of the settings stored in the library being stored in the memory of the computer, wherein the real-time sequencer is configured to send requests to the Direct Memory Access controller to recover said addresses from the computer in real time, and the real-time sequencer is configured to recover settings from the memory of the digital acquisition board by indirection based on said addresses.

7. The ultrasound imaging system according to claim 6, wherein at least one library stored in the digital acquisition board comprises at least one of a library of waveforms for ultrasound emission, and a library of filters coefficients for received signals filtering.

8. The ultrasound imaging system according to claim 1, wherein the real-time sequencer comprises a single ASIC or FPGA including a software programmable processor.

9. The ultrasound imaging system according to claim 1, wherein the memory of the computer further stores the digital data converted by the electronic circuits.

10. The ultrasound imaging system according to claim 1, wherein the memory of the computer stores beamforming parameters, and the processor of the computer is configured to perform the beamforming of the digital data.

11. The ultrasound imaging system according to claim 1, wherein the at least one Direct Access Memory controller comprises one data import engine configured to import data from the memory of the computer by implementation of the Direct Access Memory protocols, and one data export engine configured to write data in the memory of the computer by implementation of the Direct Access Memory protocols.

12. A digital acquisition board, for use in an ultrasound imaging system including an ultrasound probe having a plurality of transducers configured to emit and receive an ultrasound wave inside a region of a body, and a computer connected to and separate from the digital acquisition board and configured to visualize an image representing a portion of a medium, the computer including a processor and a memory storing respective working parameters and sequence parameters of a plurality of respective imaging modes, the digital acquisition board being configured to be disposed between the ultrasound probe and the computer, the digital acquisition board comprising:

electronic circuits configured to control the transducers to emit ultrasound waves and to convert signals sensed by transducers into digital data;

a real-time sequencer configured to store a selected imaging mode of the plurality of imaging modes, and control the electronic circuits to drive the emission and reception of ultrasound signals, based on the working parameters of the electronic circuits and the sequence parameters regulating timing of the emission and reception of the ultrasound signals of the selected imaging mode, the working parameters comprising emission parameters related to the control of the transducers for the emission of the ultrasonic waves and reception parameters related to processing of received ultrasound waves sensed by the transducers for the selected imaging mode;

at least one Direct Memory Access controller configured to access the memory of the computer in reading and writing by implementation of Direct Memory Access protocols; and at least one buffer memory, wherein the real-time sequencer is configured to send requests to the Direct Memory Access controller to cause the Direct Memory Access controller to recover a portion of the working parameters and the sequence parameters related to the selected imaging mode that are stored in the memory of the computer directly from the memory of the computer in real time without involving the processor of the computer, temporarily store the recovered portion of the working parameters and the sequence parameters of the selected imaging mode in the at least one buffer memory of the digital acquisition board, and transmit the temporarily stored working and sequence parameters of the selected imaging mode from the at least one buffer memory of the digital acquisition board to the electronic circuits, wherein the temporarily stored working and sequence parameters stored in the at least one buffer memory are overwritten by subsequent working and sequence parameters recovered from the memory of the computer by the DMA controller.

13. An ultrasound imaging process implemented by the ultrasound imaging system according to claim 1, the ultrasound imaging process comprising:

sending, by the real-time sequencer, a request to the Direct Memory Access Controller to recover the working parameters and the sequence parameters of the selected imaging mode corresponding to alternative emission and reception sequences; and prior to each of the emission sequences, sending, by the real-time sequencer, a request to the Direct Memory Access Controller to recover the working parameters and the sequence parameters corresponding to subsequent emission and reception sequences in real time from the memory of the computer.

14. The ultrasound imaging process according to claim 13, further comprising:

changing the settings of the selected imaging mode during operation of the ultrasound imaging system, and recovering, by the real-time sequencer, corresponding parameters prior to the subsequent emission sequence.

15. The ultrasound imaging process according to claim 13, wherein the computer further comprises a controller, and the process further comprises performing beamforming, by the controller, of the data received and processed by the digital acquisition board.

* * * * *